US00PP09119P

United States Patent [19]

Schofield

[11] Patent Number: Plant 9,119

[45] Date of Patent: Apr. 25, 1995

[54] LAVANDULA PLANT NAMED BLUE CUSHION

[75] Inventor: Joan I. Schofield, Bildeston, England

[73] Assignee: Blooms of Bressingham Ltd., Norfolk, United Kingdom

[21] Appl. No.: 268,126

[22] Filed: Jul. 6, 1994

[51] Int. Cl.[6] ..... A01H 5/00

[52] U.S. Cl. ..... Plt./54.1

[58] Field of Search ..... Plt. 54.1, 68.1

*Primary Examiner*—James R. Feyrer

*Attorney, Agent, or Firm*—Foley & Lardner

[57] ABSTRACT

A new and distinct Lavandula plant named 'Blue Cushion', characterized by its dwarf compact habit, profuse blooming in early June continuous into late summer, upstanding flower spikes appearing well above the foliage, and its deep blue flowers which fade first to pale blue and then to grey, giving a distinctive bicolor effect.

2 Drawing Sheets

The present invention related to a new and distinct dwarf or semi-dwarf variety of evergreen shurb of the genus Lavandula and species *L. Angustifolia.* The genus is a member of the Labiato or Lavender family, with Lavender being the common name. The new cultivar is known by the cultivar name 'Blue Cushion'.

The new cultivar is the result of a breeding program carried out by the inventor Joan Isabelle Schofield in Whatfield, Ipswich, England. The female parent was the well-known *Lavandula angustifolia* cultivar named 'Hidcote', characterized by its deep purple-blue flowers, compact and relatively slow growth habit, profuse flowering and grey-green foliage.

The female parent was the *Lavandula angustifolia* cultivar named 'Nana Alba', principally characterized by its compact dwarf habit.

'Blue Cushion' was discovered and selected as one flowering plant within the progeny of the stated cross by the inventor in a controlled environment in Whatfield, Ipswich, England. The first act of asexual propagation was accomplished when vegetative cuttings were taken from the initial selection by the inventor in Whatfield, Ipswich, England. That and subsequent propagation of the new cultivar have shown that the unique combination of characteristics as herein disclosed for 'Blue Cushion' are firmly fixed and are retained through successive generations of asexual reproduction.

'Blue Cushion' is unique in several respects. It has deeper blue flowers than is usual in the Lavandulas tending to dwarf habit. These dwarf-tending Lavandulas are further characterized as most often having short flower spikes in relation to the size of the shrub so that the flowering plant appears to lack continuity. By contrast, 'Blue Cushion' is a profuse bloomer with relatively long flower spikes, thereby presenting the appearance of an entire shrub being in synchronous heavy bloom rather than showing irregularly distributed blossom spikes. Further, the habit of 'Blue Cushion' is distinct in that it has the upright characteristics of a taller growing variety with many flower spikes appearing well above the foliage. This is in contrast to other dwarf Lavandulas that in many cases have short uneven flowering spikes. The deep blue flower spikes of 'Blue Cushion' appear in profusion in early June and continue with several flushes giving the appearance of continual flowering, sometimes as late as September. Other Lavandulas of similar size tend to have an uneven flowering habit giving an untidy appearance. As the flowers of 'Blue Cushion' mature, they fade to pale blue and then to grey producing an unusual bicolor effect. Continuity of flowering is encouraged by removal of dead flower spikes.

'Blue Cushion' has not been observed under all possible environmental conditions. The phenotype may vary somewhat with variations in environment such as temperature, light intensity and daylength, without, however, any variance in genotype.

The following observations, measurements and comparisons describe plants grown in Whatfield, Ipswich, England and Bressingham, Diss, Norfolk, England.

The accompanying photographic drawings show typical inflorescence and leaf characteristics of 'Blue Cushion', with the colors being as nearly true as possible with illustrations of this type.

Sheet 1 is a close-up color photograph of 'Blue Cushion'.

The photo on Sheet 2 shows a bed of plants of 'Blue Cushion' in a typical garden setting.

In the following detailed description color references are made to The Royal Horticultural Society Colour Chart. The color values and other data are based on plant material grown in Bressingham, Diss, Norfolk, England.

Classification:

*Origin.*—Seedling selection.

*Parentage.*—A cross between *Lavandula angustifolia* 'Hidcote' and *Lavandula angustifolia* 'Nana Alba'.

Plant:

*Habit.*—Dwarf rounded habit, compact; ideal for use in borders or in containers.

*Size.*—Mature plants are about 160 mm tall with a spread of about 400 mm.

*Root system.*—Fibrous, becoming woody.

*Plant vigor.*—The shrub shows vigorous and healthy growth throughout Great Britain.

*Blooming habit.*—Prolific. Entire shrub covered with a dense mass of blossom spikes.

*Blooming period.*—Early June continuous into late summer.

*Hardiness.*—Winter hardy throughout the British Isles. The plant has not been tested for extended maximum summer temperature tolerance above 90° F.

Foliage:

*Arrangement.*—Stiff, alternate and opposite on brownish wiry stems.

*Type.*—Evergreen leaves on woody shrub.

*Texture.*—Dull, upper surface very slightly hairy, lower surface slightly hairy.

*Shape.*—Linear.

*Length.*—About 15 mm.

*Width.*—About 2 mm.

*Petiole.*—Absent.

*Margins.*—Entire.

*Apex.*—Obtuse.

*Base.*—Truncate.

*Color.*—Mature leaves, upper surface 137B, lower surface 137C.

Flowers:

*Petal count.*—Four.

*Petal shape.*—Elliptic.

*Flower type.*—Joined at base in short tube. Zygomorphic.

*Carpels.*—Very small.

*Stamens.*—Very small.

*Blooming habit.*—Approximately 30 flowers in axillary racemes, some branched.

*Blooming period.*—Early June continuing into late summer.

*Color.*—When flowers are just fully opened, color is deep blue 97A; flowers fade first to 97C and then to greyed-green 196D. Because flowers of varying maturity appear on the plant at the same time, the various described colors give an unusual bicolor effect.

It is claimed:

1. A new and distinct Lavandula plant named 'Blue Cushion', as illustrated and described.

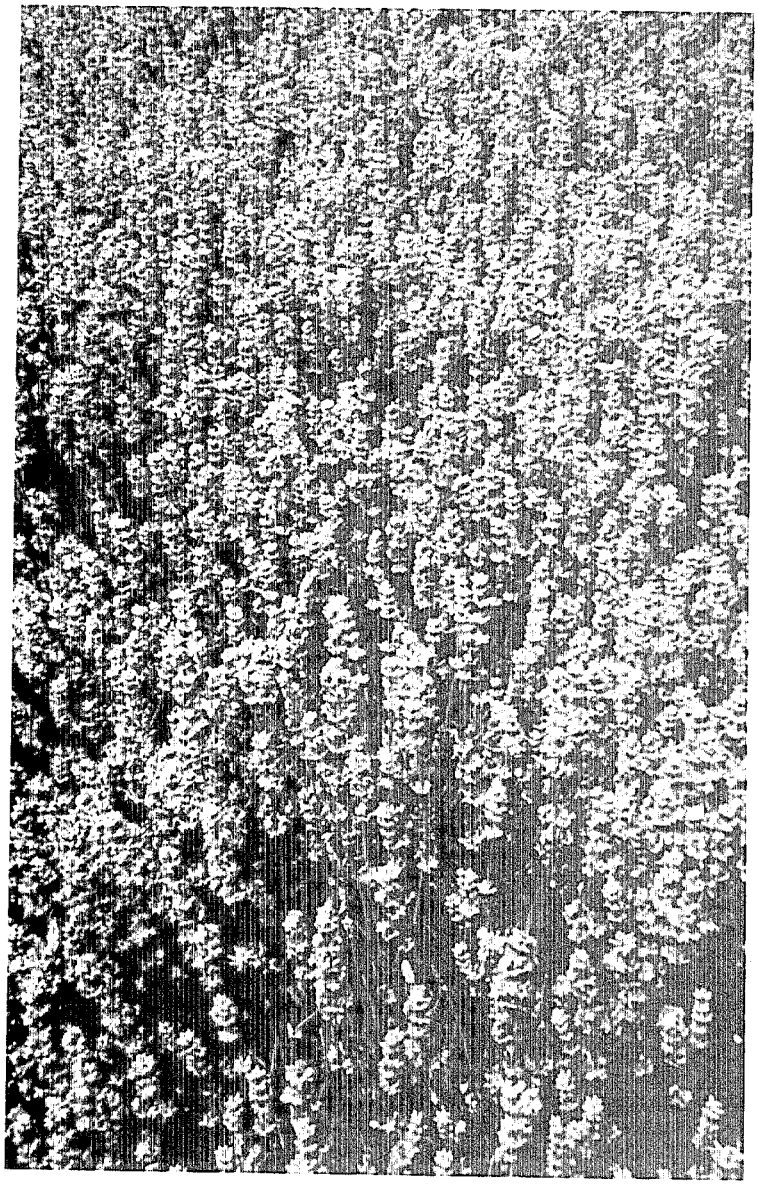

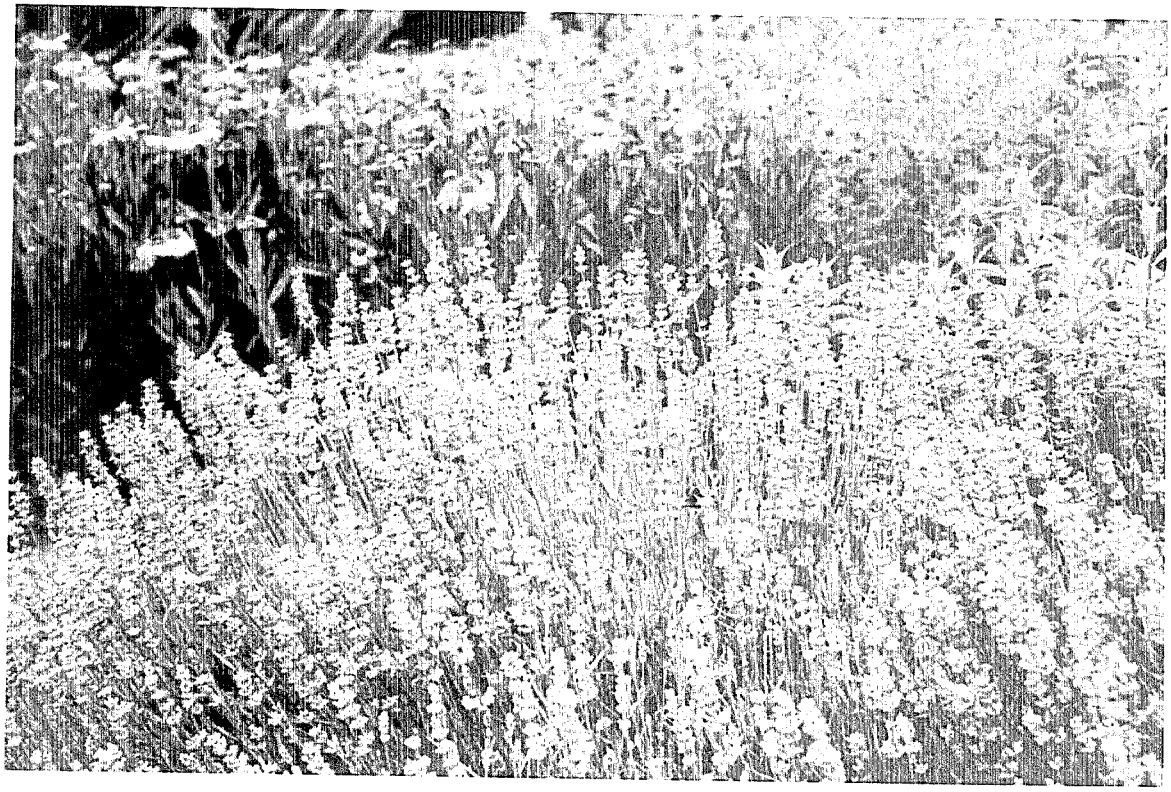

* * * * *